United States Patent [19]

Henshaw

[11] Patent Number: 4,513,441
[45] Date of Patent: Apr. 23, 1985

[54] IMAGE COMPARISON SYSTEM

[75] Inventor: Philip D. Henshaw, Lexington, Mass.

[73] Assignee: Sparta, Inc., Lexington, Mass.

[21] Appl. No.: 519,736

[22] Filed: Aug. 2, 1983

[51] Int. Cl.³ .................... G01N 21/32; G06K 9/00
[52] U.S. Cl. ................................ 382/43; 250/550;
250/562; 350/162.12; 356/237; 382/31
[58] Field of Search .............. 382/31, 43; 250/550,
250/562, 563, 572; 356/237, 239; 350/162.12,
162.13, 162.14, 162.11; 358/106; 364/507, 576,
724–726, 825–826; 343/5 FT, 5 MM

[56] References Cited

U.S. PATENT DOCUMENTS

| 4,084,255 | 4/1978 | Casasent et al. | 382/43 |
| 4,282,510 | 8/1981 | Southgate | 382/31 |
| 4,282,511 | 8/1981 | Southgate et al. | 382/31 |
| 4,330,775 | 5/1982 | Iwamoto et al. | 382/31 |
| 4,360,269 | 11/1982 | Iwamoto et al. | 350/162.12 |

Primary Examiner—Leo H. Boudreau
Attorney, Agent, or Firm—Joseph S. Iandiorio

[57] ABSTRACT

Image comparison is accomplished by forming a composite image composed of a reference image and a test image. A two-dimensional image spectrum is generated from the composite image and then is whitened by setting the magnitude of every point of the two-dimensional image spectrum to a uniform level. A phase-only image of the composite image is then constructed, and values of the phase-only image exceeding a predetermined threshold are detected as an indication of the location of a difference between the reference and test images.

16 Claims, 16 Drawing Figures

IMAGE COMPARISON SYSTEM

FIELD OF INVENTION

This invention relates to an image comparison system, and more particularly to such a system which detects extreme levels in a phase-only image to locate differences between a test image and a reference image.

BACKGROUND OF INVENTION

Image comparison methods and equipment are widely used in manufacturing, testing, surveillance and many other applications. Current techniques of image comparison include image subtraction, color overlay and image flashing or alternating. Image subtraction algebraically combines the magnitude of each point or pixel of the reference image and test image so that like parts cancel and only differences remain. In the color overlay approach, each image is filtered with a different color so that differences appear in one or the other color and like parts appear as a blend of both colors. In image flashing, first one and then the other image is flashed on a screen: like parts remain steady; differences blink. However, these methods have a number of shortcomings and may fail or give poor results because of image-to-image misregistration and differences in overall intensity levels of the two images.

SUMMARY OF INVENTION

It is therefore an object of this invention to provide a comparison system and method which is insensitive to misregistration between test and reference images.

It is a further object of this invention to provide such a system and method which is insensitive to differences in overall intensity levels between the reference and test images.

It is a further object of this invention to provide such a method and system in which the image data is normalized and permits the use of a universal threshold to detect differences between the test and reference images.

The invention results from the realization that by forming a composite image from a reference and test image, the like parts of the two images become periodic and so can be easily suppressed in a phase-only image while the unlike parts are aperiodic and thus easily detected.

The invention features an image comparison system having means for forming a composite image composed of a reference image and a test image. There are means for generating a two-dimensional image spectrum from the composite image and means for whitening the two-dimensional image spectrum by setting the magnitude of every point of the two-dimensional image spectrum to a uniform level. There are means responsive to the means for whitening to construct the phase-only image of the composite image, and there are means for detecting a value of the phase-only image exceeding a predetermined threshold which is representative of the location of a difference between the reference and the test images.

In a preferred embodiment, the means for forming may include an image buffer for combining the reference and test images into the composite image. A sensor may be used for obtaining one or both of the reference and test images. A storage device may also be used for storing one or both of the reference and test images. The image buffer may include an optical storage means. The means for generating may include a transform circuit, which may be a Fourier transform circuit, a Fast Fourier transform circuit, a Hadamard transform circuit, or a similar transform circuit. The means for generating may instead include optical means, such as a lens.

The means for whitening may include means for normalizing the complex components at each point of the two-dimensional image. The means for constructing may include an inverse transform circuit, such as a Fourier, Fast Fourier, Hadamard, or any other transform circuit as previously indicated. In certain transformations, such as those using the Hadamard approach, each point of the phase-only image may have a phase of either zero or 180 degrees.

The invention also features a method of image comparison, which includes forming a composite image composed of a reference image and a test image and generating a two-dimensional image spectrum from the composite image. The two-dimensional image spectrum is then whitened by setting the magnitude of every point of the two-dimensional image spectrum to a uniform level. The phase-only image of the composite image is then constructed. Finally, values of the phase-only image exceeding a predetermined threshold are detected representative of the location of a difference between the reference and test image.

DISCLOSURE OF PREFERRED EMBODIMENT

Other objects, features and advantages will occur from the following description of a preferred embodiment and the accompanying drawings, in which.

Figure 1:
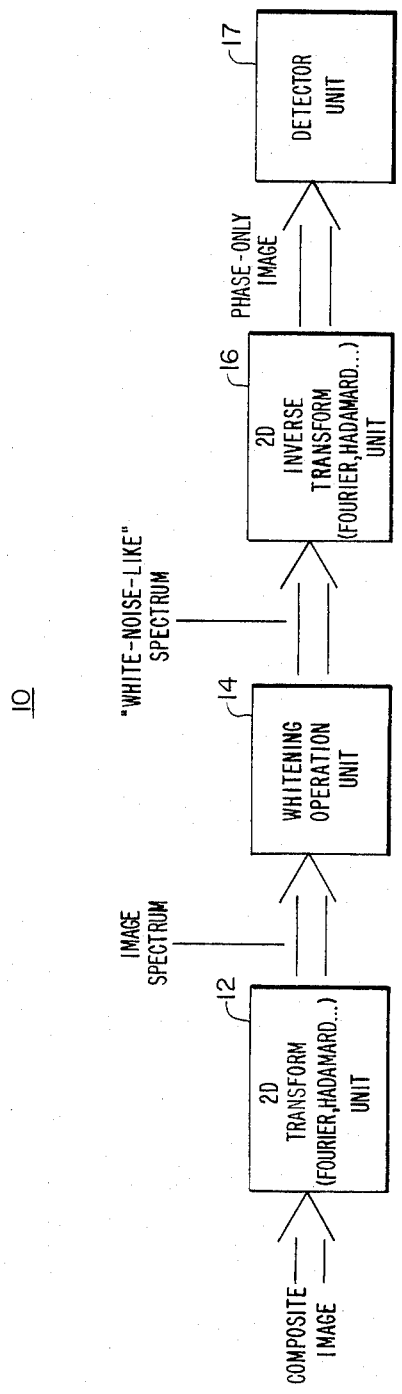
FIG. 1 is a block diagram of an image comparison system according to this invention.
Figure 2:
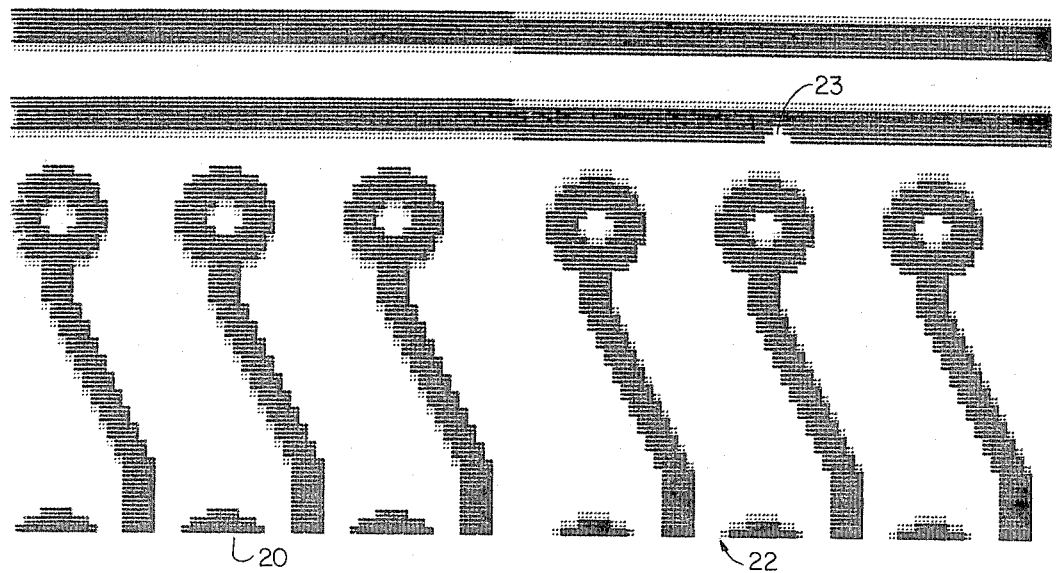
FIG. 2 is an illustration of a composite image including a reference image and a test image.
Figure 9:
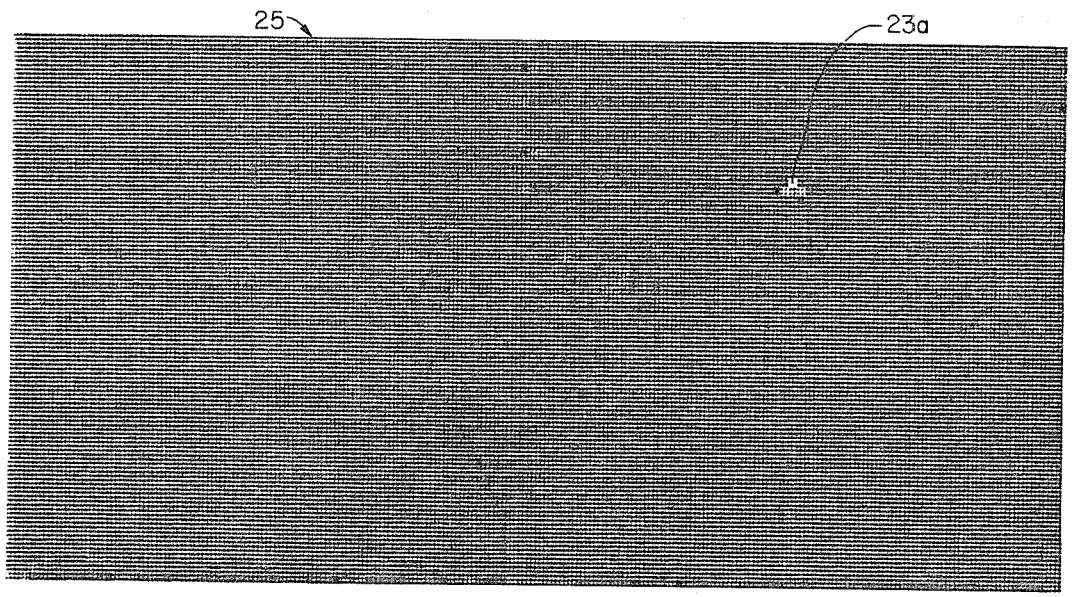
FIG. 9 is a representation of the phase-only image of the reference and test images.

There is shown in FIG. 1 an image comparison system 10 according to this invention which includes a two-dimensional transform unit 12, a whitening operation unit 14, a two-dimensional inverse transform unit 16 and a detection unit 17. A composite image 18, FIG. 2, composed of a reference image 20 and test image 22, is fed into the two-dimensional transform unit 12. There a transform is made of the image using Fourier, Fast Fourier, Hadamard, or other techniques, such as cosine, M-sequence or others, using either cartesian or polar coordinates. The image spectrum thereby produced is delivered to the whitening operation unit 14, where the magnitude of each point of the image spectrum is normalized to produce a uniform level of amplitude and produce a white noise-like spectrum. The white noise-like spectrum is then submitted to the two-dimensional inverse transform unit 16, which again performs according to a known transform technique such as the Fourier, Hadamard or any of the others previously listed with respect to unit 12. The phase-only image at the output of two-dimensional inverse transform unit 16 is delivered to detector unit 17, which compares each of the image point or pixel values to a reference threshold and responds to those that exceed that threshold as an indication of a difference between the reference image 20 and test image 22. For example, the defect 23 in test image 22, FIG. 2, appears at position 23a in the phase-only image 25, FIG. 9, which appears at the output of inverse transform unit 16. In this inverse transform operation the phase-only image of the original composite image is constructed. It is a phase-only image because the amplitude levels have been eliminated in the whitening operation and only the phase angle of the information relating to each point in the image spectrum still remains.

Figures 3, 4:
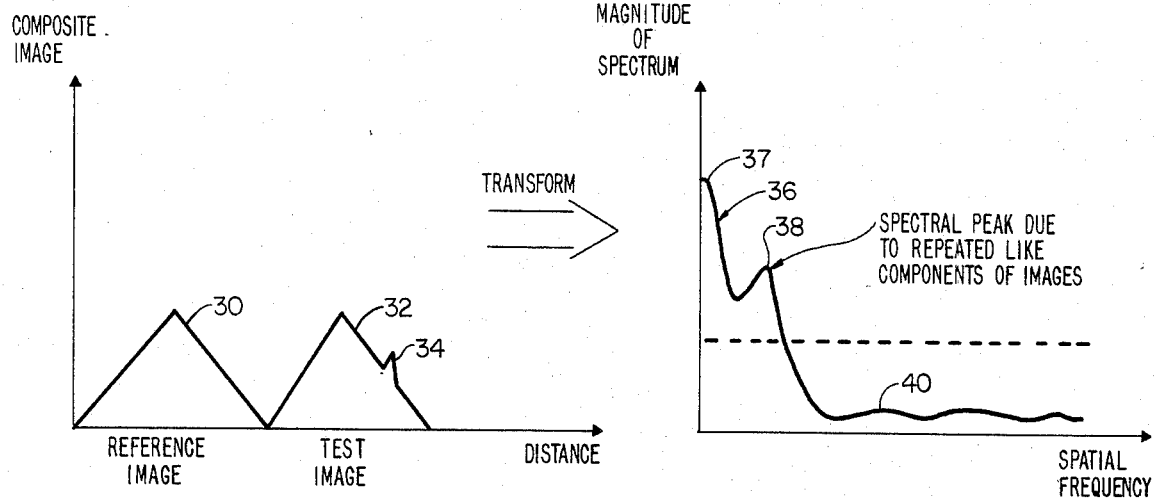
FIG. 3 is a graphical illustration of one slice of a reference image and test image making up a composite image.
FIG. 4 is an illustration of the characteristic spectrum of the transformed composite image.
Figures 5, 6:
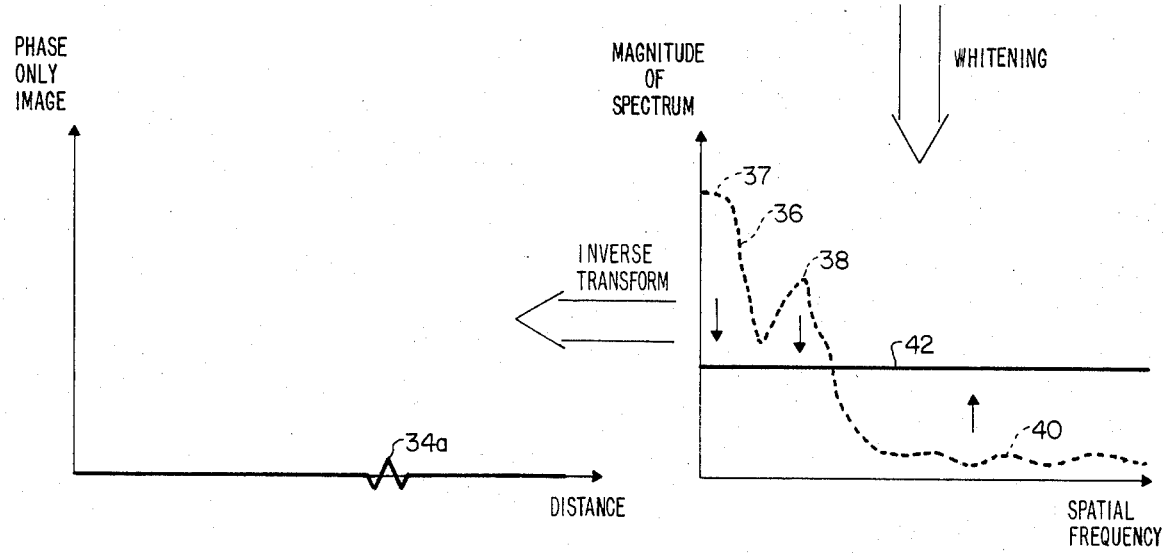
FIG. 5 is an illustration of the image after whitening by normalization.
FIG. 6 is an illustration of the phase-only image.

The processing of the composite image through system 10 to the final phase-only image is depicted in FIGS. 3–6, where a slice through the composite image is represented, FIG. 3, by two triangular wave shapes 30, 32, which represent the reference image and test image respectively. The test image has a defect 34. After the first transform operation by two-dimensional transform unit 12, the image spectrum appears as shown in FIG. 4, where the spectral characteristic 36 has a peak 38 due to the repeated like components of the images, and the defect 34 is typically contained in the higher frequency extent 40 of characteristic 36. Peak 37 is derived from the average level of the composite image. It is the periodicity reflected by wave shapes 30 and 32 that enables the use of the phase-only image technique to detect defects. Following this, in the whitening step, characteristic 36, FIG. 5, is normalized, resulting in a single uniform amplitude level 42 for all of the points in the spectrum. Thus, peaks 37 and 38 have been decreased and the lower area of higher frequency derivation has been increased. Inverse transformation, FIG. 6, results in the cancellation of peaks 37, 38, and lower section 40, and the emphasizing of the defect 34 contained in the lower section 40.

Figure 7:
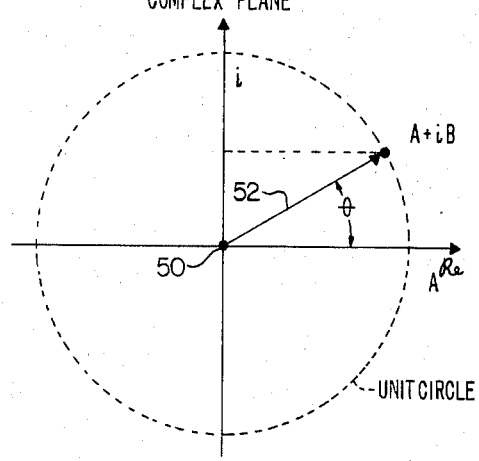
FIG. 7 is a graphical illustration of the vector representing a point or pixel of the image spectrum before whitening.
Figure 8:
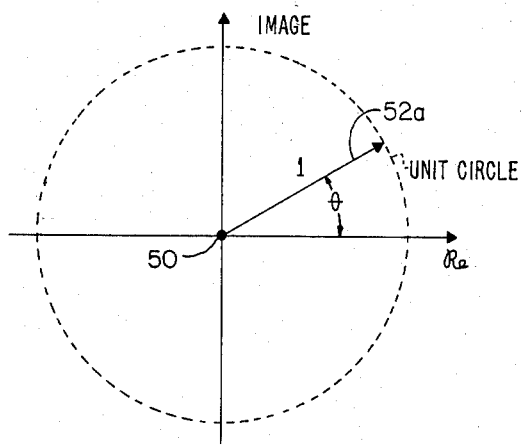
FIG. 8 is an illustration similar to FIG. 7 after normalization or whitening.

The whitening or normalizing operation can be understood by referring to FIG. 7, which illustrates the complex value of a single point 50 of the image, whose magnitude is represented by vector 52 having a real component A and an imaginary component iB. When each of those components is normalized, that is divided by $\sqrt{A^2+B^2}$, the magnitude of each of the points in the image is made uniform, for example, at unity or at some other value, as shown in FIG. 8, and the only variation then remaining is the phase angle. That is the condition pictured in FIG. 5. When applying a Hadamard transform, the whitening results in a normalization that provides only two phase angles: zero and 180 degrees. This is also known as a sign-only image, since zero and 180 may be viewed as plus and minus values.

Figure 10:
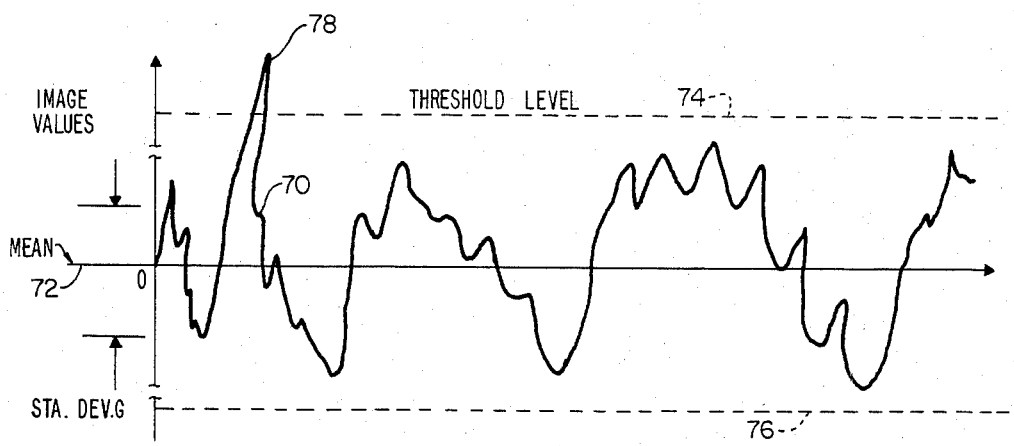
FIG. 10 is a graphical illustration of the image signal after whitening with the detector threshold levels superimposed.

Since the normalizing or whitening operation effects a white noise-like spectrum output 70, FIG. 10, the mean value 72 of the output is essentially zero. The threshold, both positive and negative, 74 and 76, is then set at a level which accepts substantially all of the output signals 70 with the exception of extreme excursions, such as 78, which are interpreted as defects or differences between the test and the reference image. In one application, a threshold setting at approximately seven standard deviations provided a probability of error of one part in a million. Since the image has been normalized in the whitening process, the threshold level will be the same for all images of the same size, that is having the same number of pixels, and thus a universal threshold level can be used to apply to all applications of the system.

Figure 11:
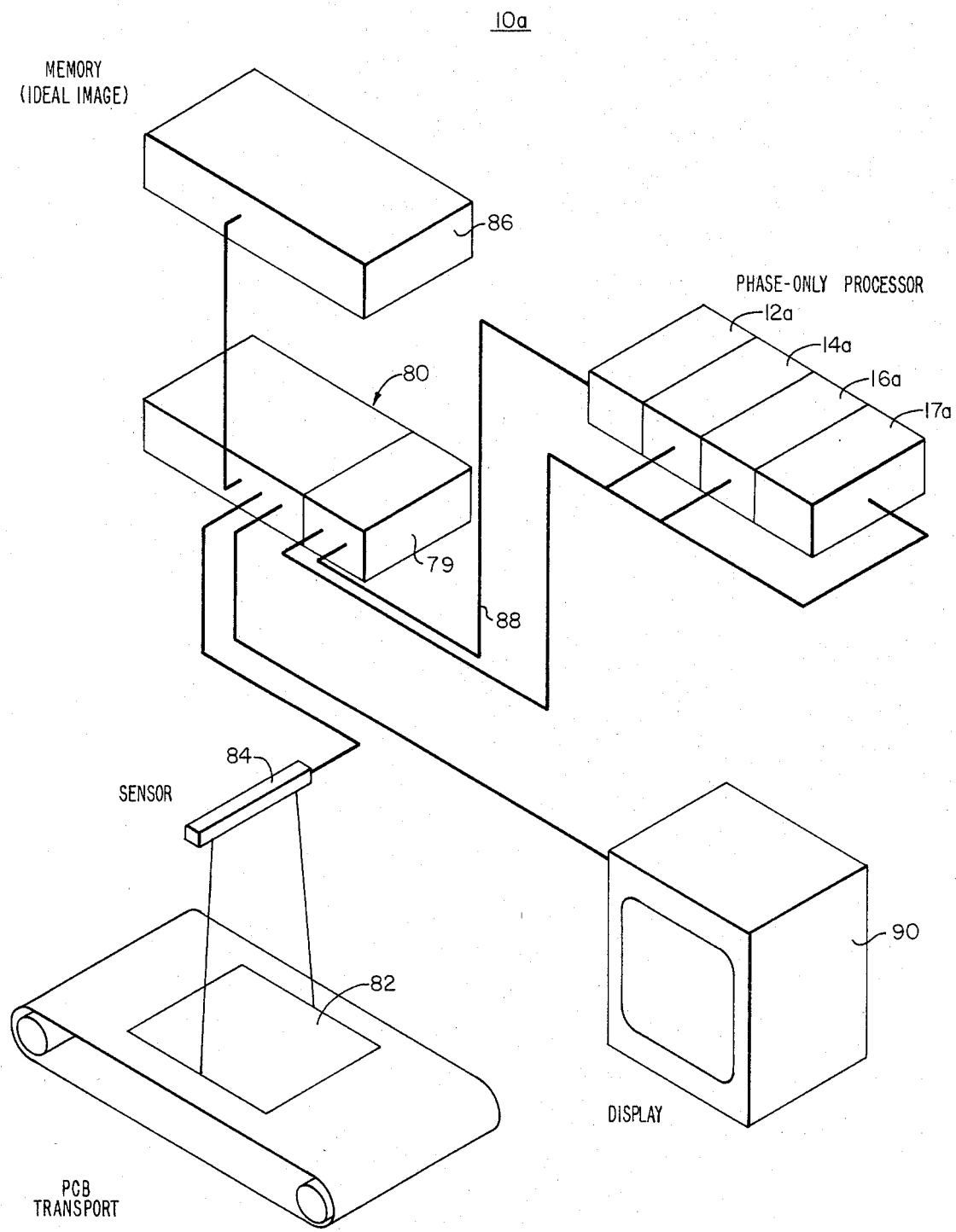
FIG. 11 is a block diagram of an electronic implementation of the image comparison system according to this invention.

In one construction, an essentially electronic implementation of the image comparison system 10a, FIG. 11, according to this invention may be made using a control computer 80, using, for example, an Intel 8086 microprocessor, and having an image buffer 79 for receiving the test image 82 from sensor 84 and forming it into a composite image in conjunction with the reference image from memory 86. Throughout the figures, like parts are given like numbers and similar parts like numbers accompanied by successive lower case letters. The composite image is then delivered by computer 80 over line 88 to two-dimensional transform unit 12a, where the composite image is processed as previously explained with respect to FIGS. 1–10. The phase-only image from unit 16 or the detection information 17 may then be fed back to computer 80 for processing or display on monitor 90. Although in FIG. 11 the reference image is illustrated as stored in memory 86 and test image 82 is presented through sensor 84, this is not a necessary limitation of the invention. For example, their sources could be interchanged, or both could be provided through memory, or both provided through an input sensor.

Figure 12:
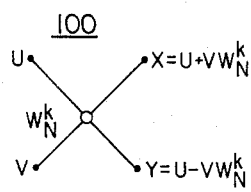
FIG. 12 is a schematic representation of the implementation of the two-dimensional transform unit of FIG. 11.
Figure 13:
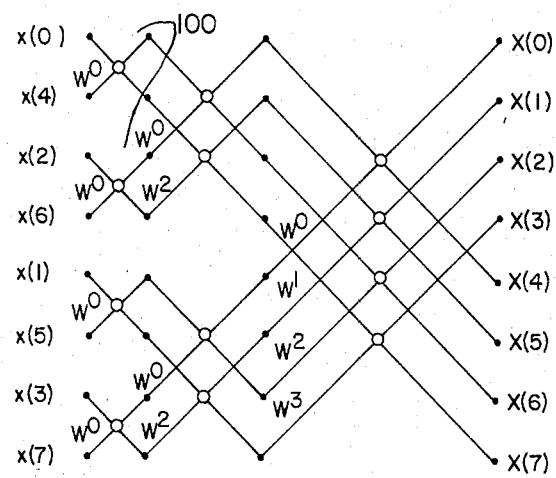
FIG. 13 is a schematic showing a network of circuits such as shown in FIG. 12.

Two-dimensional transform unit 12a may be implemented with a standard butterfly circuit 100, FIG. 12, which when used to perform a fast Fourier transform receives pixel signals U, V at its inputs, multiplies the V signal by the complex number $W^k_N$, and obtains at its output X and Y, where $X = U + VW^k_N$, and $Y = U - VW^k_N$. Butterfly circuit 100 may be used in groups, as shown in FIG. 13, to increase the speed of processing. Such circuits are fully explained in *Theory and Application of Digital Signal Processing*, L. R. Rabiner and B. Gold, Prentice-Hall, Englewood Cliffs, New Jersey, 1975.

Figure 14:
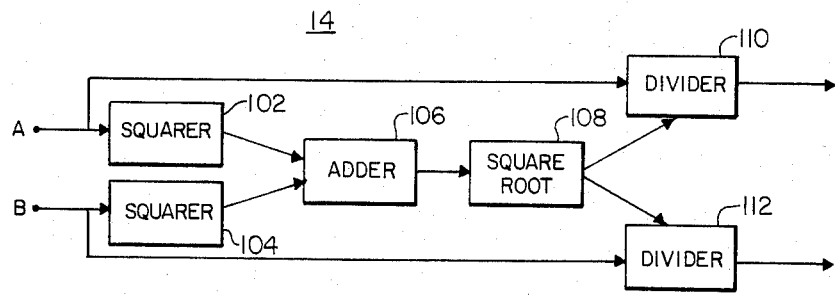
FIG. 14 is a more detailed block diagram of the whitening unit of FIG. 11.

The normalization process which occurs in whitening operation unit 14, as explained in FIG. 7 and 8, employs squarer circuits 102 and 104, FIG. 14, to square the A and B values in adder 106 to combine those values. The combined value at the output of adder 106 is then submitted to square root circuit 108, whose output is submitted to divider circuit 110 as the divisor for the value A and divider 112 as the divisor for value B, which results in the uniform value for vector 52a of FIG. 8.

Figure 15:
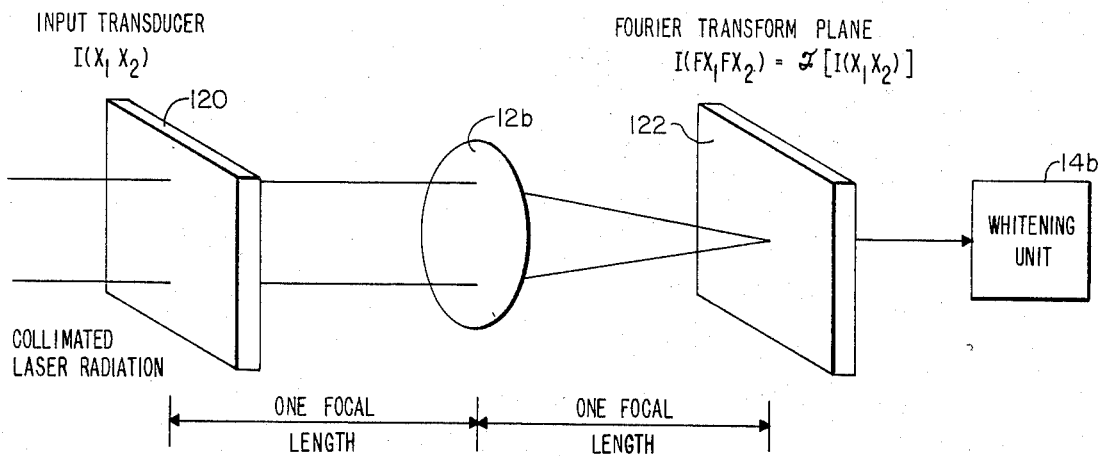
FIG. 15 is an optical implementation of the image comparison system of this invention.

In FIG. 11, in the electronic implementation of the image comparison system of FIG. 1, the means for forming a composite image includes image buffer 79 in computer 80. Alternatively, in an optical implementation, FIG. 15, the composite image may be formed in an optical input transducer 120 such as a liquid crystal or on a frame of film. The composite image is delivered to the two-dimensional transform unit 12b, which may consist simply of a lens, which transforms and projects the composite image as a Fourier transform in the Fourier transform plane 122. Subsequently, the image spectrum at the Fourier transform plane 122 may be normalized in a whitening operation unit 14b and then resubmitted to lens 12b or a similar lens for the inverse Fourier transformation, after which detection may be accomplished.

Figure 16:
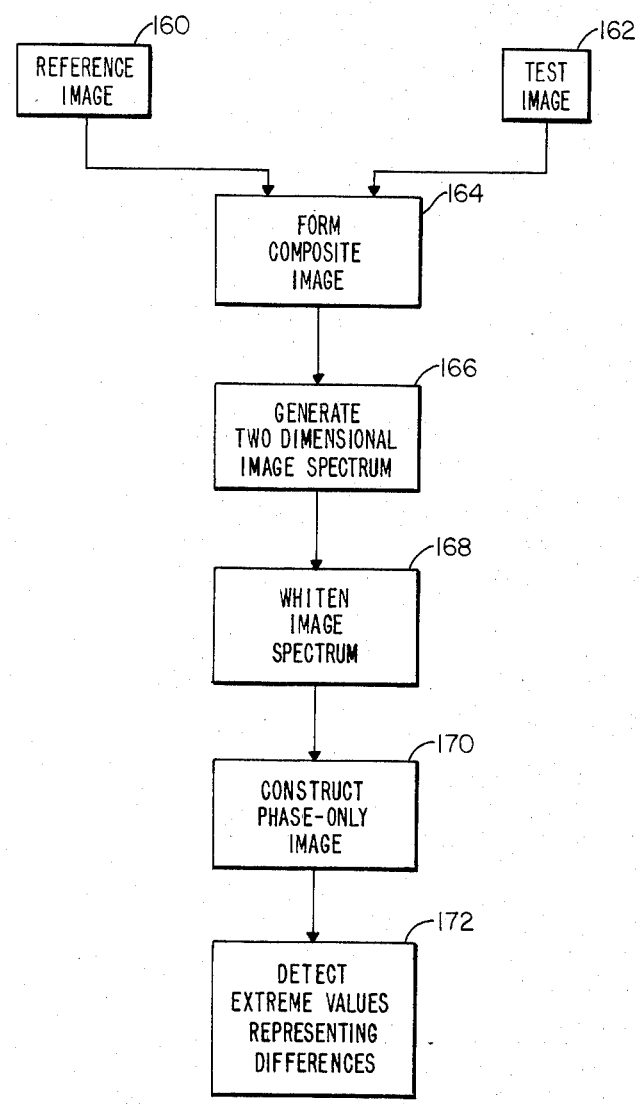
FIG. 16 is a diagram showing the method of this invention.

A simple and straightforward understanding of the method of this invention may be understood with respect to FIG. 16, where the reference image 160 and test image 162 are delivered and formed into a composite image in step 164. Following that, there is generated in step 166 a two-dimensional image spectrum from the composite image. Then the image spectrum is whitened in step 168 and a reverse transform is performed to construct the phase-only image in step 170 from the whitened image spectrum. Finally, extreme values of amplitude are detected from the phase-only image to determine differences between the reference image and the test image in step 172.

Other embodiments will occur to those skilled in the art and are within the following claims:

What is claimed is:

1. An image comparison system comprising:
   means for forming a composite image composed of a reference image and a test image;
   means for generating a two-dimensional image spectrum from said composite image;
   means for whitening said two-dimensional image spectrum by setting the magnitude of every point of the two-dimensional image spectrum to a uniform level;
   means, responsive to said means for whitening, for constructing the phase-only image of said composite image; and
   means for detecting a value of the phase-only image exceeding a predetermined threshold representative of the location of a difference between the said reference and test images.

2. The image comparison system of claim 1 in which said means for forming includes an image buffer for combining said reference and test images into said composite image.

3. The image comparison system of claim 1 in which said means for forming includes a sensor for obtaining at least one of said reference and test images.

4. The image comparison system of claim 1 in which said means for forming includes a storage device for storing at least one of said reference and test images.

5. The image comparison system of claim 2 in which said image buffer includes optical storage means.

6. The image comparison system of claim 1 in which said means for generating includes a transform circuit.

7. The image comparison system of claim 6 in which said transform circuit is a Fourier transform circuit.

8. The image comparison system of claim 6 in which said transform circuit is a Hadamard transform circuit.

9. The image comparison system of claim 6 in which said mans for generating includes optical means.

10. The image comparison system of claim 9 in which said optical means includes a lens.

11. The image comparison system of claim 1 in which said means for whitening includes means for normalizing the complex components of each point of the two-dimensional image.

12. The image comparison system of claim 1 in which said means for constructing includes an inverse transform circuit.

13. The image comparison system of claim 12 in which said inverse transform circuit is an inverse Fourier transform circuit.

14. The image comparison system of claim 12 in which said inverse transform circuit is an inverse Hadamard transform circuit.

15. The image comparison system of claim 14 in which each point of said phase-only image has a phase of either zero or one hundred and eighty degrees.

16. An image comparison method comprising:
   forming a composite image composed of a reference image and a test image;
   generating a two-dimensional image spectrum from said composite image;
   whitening said two-dimensional image spectrum by setting the magnitude of every point of the two-dimensional image spectrum to a uniform level;
   constructing the phase-only image of the composite image; and
   detecting a value of the phase-only image exceeding a predetermined threshold representative of the location of a difference between said reference and test images.

* * * * *